(12) United States Patent
Magno (10) Patent No.: US 11,777,375 B2
(45) Date of Patent: Oct. 3, 2023

(54) HANDHELD SURGICAL INSTRUMENT WITH HEAT MANAGEMENT

(71) Applicant: GYRUS ACMI, INC., Southborough, MA (US)

(72) Inventor: Joey Magno, Cordova, TN (US)

(73) Assignee: Gyrus ACMI, Inc., Westborough, MA (US)

( * ) Notice: Subject to any disclaimer, the term of this patent is extended or adjusted under 35 U.S.C. 154(b) by 336 days.

(21) Appl. No.: 17/004,111

(22) Filed: Aug. 27, 2020

(65) Prior Publication Data

US 2021/0104938 A1   Apr. 8, 2021

Related U.S. Application Data

(60) Provisional application No. 62/910,633, filed on Oct. 4, 2019.

(51) Int. Cl.
*H02K 9/00* (2006.01)
*H02K 9/22* (2006.01)
*A61B 17/16* (2006.01)
*A61B 17/32* (2006.01)
*A61B 17/00* (2006.01)

(52) U.S. Cl.
CPC ........... *H02K 9/22* (2013.01); *A61B 17/1628* (2013.01); *A61B 17/32* (2013.01); *A61B 17/1679* (2013.01); *A61B 17/1688* (2013.01); *A61B 2017/00398* (2013.01)

(58) Field of Classification Search
CPC ...... H02K 9/22; A61B 17/1628; A61B 17/32; A61B 17/1679; A61B 17/1688; A61B 2017/00398; A61B 2217/005; A61B 17/24; A61B 17/32002; A61B 17/1622
See application file for complete search history.

(56) References Cited

U.S. PATENT DOCUMENTS

| 4,759,349 A | 7/1988 | Betz et al. |
| 5,543,695 A | 8/1996 | Culp et al. |
| 8,388,523 B2 | 3/2013 | Vivenzio et al. |

(Continued)

FOREIGN PATENT DOCUMENTS

| DE | 102018203314 A1 * | 9/2019 |
| EP | 3524188 A2 | 8/2019 |
| KR | 20100058206 A | 6/2010 |
| WO | WO-2011085392 A1 | 7/2011 |

OTHER PUBLICATIONS

CN 108075605 A (Year: 2018).*

(Continued)

*Primary Examiner* — Ahmed Elnakib
*Assistant Examiner* — Elrasheed E. B. Hamdan
(74) *Attorney, Agent, or Firm* — Schwegman Lundberg & Woessner, P.A.

(57) ABSTRACT

A handpiece for a handheld surgical instrument having a motor and a heatsink is provided. The motor is within a motor housing and the heat sink is disposed around and thermally coupled with the motor housing. The handpiece is formed from a material having a first thermal conductivity and the heat sink has a second thermal conductivity that is greater in value than the first thermal conductivity of the material of the handpiece. The heat sink is configured to dissipate heat from the motor during operation of the motor to the handpiece.

18 Claims, 7 Drawing Sheets

(56) References Cited

U.S. PATENT DOCUMENTS

| | | | |
|---|---|---|---|
| 9,072,874 B2 | 7/2015 | Northrop et al. | |
| 9,451,976 B2 | 9/2016 | Schneider et al. | |
| 10,178,997 B2 | 1/2019 | Edwards | |
| 10,660,624 B2* | 5/2020 | Chon | A61B 17/1626 |
| 2002/0165549 A1* | 11/2002 | Owusu-Akyaw | A61B 17/1628 606/80 |
| 2008/0195066 A1* | 8/2008 | Speeg | A61B 10/0275 604/326 |
| 2014/0206939 A1 | 7/2014 | Eisele et al. | |
| 2015/0201918 A1* | 7/2015 | Kumar | A61B 17/1622 606/104 |
| 2016/0081699 A1* | 3/2016 | Edwards | A61B 17/1622 606/79 |
| 2018/0078246 A1 | 3/2018 | Chon et al. | |
| 2018/0132889 A1 | 5/2018 | Batchelor et al. | |

OTHER PUBLICATIONS

DE 102018203314 A1 (Year: 2019).*
"Diego Elite Efficiency and Choice—the Olympus Rhinology Shaver System EN 8226", (2020), 5 pgs.
"Diego Elite Handpiece Cleaning Quick-Reference Guide EN 8268", (2020), 2 pgs.
"Diego-Elite Setup and Operation Quick-Reference Guide GB 8402", (2020), 4 pgs.
"European Application Serial No. 20196528.2, Communication Pursuant to Article 94(3) EPC dated Mar. 29, 2021", 5 pgs.
"European Application Serial No. 20196528.2, Extended European Search Report dated Mar. 17, 2021", 4 pgs.
"Therma-Tech TT6600-5004 El White—Polyamide 66", Technical Data Sheet. PolyOne Corporation, (2019), 2 pgs.
"Therma-Tech TT9200-5001 El White—Polyphenylene Sulfide", Technical Data Sheet. PolyOne Corporation, (2019), 2 pgs.
"Therma-Tech TT9200-5003 EC MID Anthracite—Polyphenylene Sulfide", Technical Data Sheet. PolyOne Corporation, (2015), 2 pgs.
Mezailles, Marc, et al., "Metal replacement with specialty thermoplastic solutions in heat-sensitive applications", SPE Antec, (2014), 7 pgs.
"European Application Serial No. 20196528.2, Response filed Jul. 21, 2021 to Communication Pursuant to Article 94(3) EPC dated Mar. 29, 2021", w/ English Claims, 9 pgs.
"European Application Serial No. 20196528.2, Communication Pursuant to Article 94(3) EPC dated Feb. 15, 2023", 4 pgs.
"European Application Serial No. 20196528.2, Response filed Jun. 16, 2023 to Communication Pursuant to Article 94(3) EPC dated Feb. 15, 2023", 10 pgs.

* cited by examiner

HANDHELD SURGICAL INSTRUMENT WITH HEAT MANAGEMENT

CROSS-REFERENCE TO RELATED APPLICATION

This application claims the benefit of priority to U.S. Provisional Patent Application Ser. No. 62/910,633, filed Oct. 4, 2019, the contents of which are incorporated herein by reference in their entirety.

TECHNICAL FIELD

This document pertains generally, but not by way of limitation, to surgical devices that can be used for various surgical procedures. More specifically, but not by way of limitation, the present application relates to a handheld surgical instrument.

BACKGROUND

Occlusions within cavities of patients, such as sinus cavities, can cause a number of issues with a patient. These issues can include, for example, chronic rhinosinusitis, a deviated septum, nasal polyps, or the like. In order to remove these or other types of occlusions within cavities, a physician can use a handheld surgical instrument having a microdebrider or a drill. Microdebriders can be used with a variety of implements depending on the procedure being performed. A microdebrider can include a cutting implement that can oscillate, i.e., moves in a back and forth rotational motion, and that can be used in Rhinologic procedures to remove softer tissues of the sinuses. For example, a pre-bent implement having cutting implements can be used when surgery is being performed at difficult to reach surgical sites, such as the aforementioned sinus cavities. Moreover, cutting implements that can facilitate 360-degree rotation can also be used with a single microdebrider. Thus, a single microdebrider can be used for a variety of procedures with a variety of implements. As noted above, a drill can also be used. For example, a drill can be used in Otologic procedures to remove bone in, and around, the ear.

Typically, a microdebrider and/or a drill includes a motor, such as a DC motor, coupled with a driveshaft that rotates upon activation of the DC motor. In addition, the microdebrider and/or a drill can include a handpiece, where a user holds the microdebrider or the drill at the handpiece and manipulates the microdebrider or the drill using the handpiece during a procedure. The handpiece can be formed of a material having a relatively low thermal conductivity. Moreover, the DC motor is usually positioned within the handpiece proximal to where the surgeon holds the microdebrider/drill.

As the surgeon performs a procedure, the DC motor can operate at high speed. During a procedure, such as bone removal in an Otologic procedure, the torque required by the DC motor to operate at high rpms draws great amounts of current. As may be appreciated, the increased current draw increases the heat dissipated by the DC motor during use. Since the handpiece is formed of a material having a relatively low thermal conductivity range, the handpiece can get very hot, thereby causing discomfort for a surgeon using the microdebrider/drill. In particular, a hotspot can form on the handpiece where the user holds the handpiece. In these situations, the user can be forced to stop using the microdebrider/drill until the handpiece cools sufficiently to allow holding. Thus, hot spotting may minimize the type of power that can be used with the microdebrider/drill. In other words, current designs preclude the use of motors with higher power outputs since these motors dissipate greater amounts of heat, which contribute to the problems discussed above.

Accordingly, what is needed is a handheld surgical device, such as a microdebrider or a drill, having a handpiece that is capable of dissipating heat during use of the handheld surgical device. Moreover, this handpiece should be able to dissipate heat for motors having increased power outputs.

SUMMARY

Examples of the present disclosure relate to a handpiece for a handheld surgical instrument that facilitates heat dissipation during use. In particular, examples of the present disclosure relate to a handheld surgical instrument that can include a handpiece, a motor having a motor housing, and a heat sink disposed around the motor housing.

DETAILED DESCRIPTION

Examples of the present disclosure relate to a handpiece for a handheld surgical instrument that facilitates heat dissipation during use. In particular, examples of the present disclosure relate to a handheld surgical instrument that can include a handpiece, a motor having a motor housing, and a heat sink disposed around the motor housing. The heat sink can include a plurality fins disposed along a length of the heat sink and that can radially extend from a surface of the heat sink. At least one fin of the plurality of fins can thermally couple with the handpiece. Thus, during operation of the motor, heat generated by the motor can be dissipated to the motor housing and then transferred to the heat sink. The heat can then be transferred to the handpiece via the fins.

Figure 1:
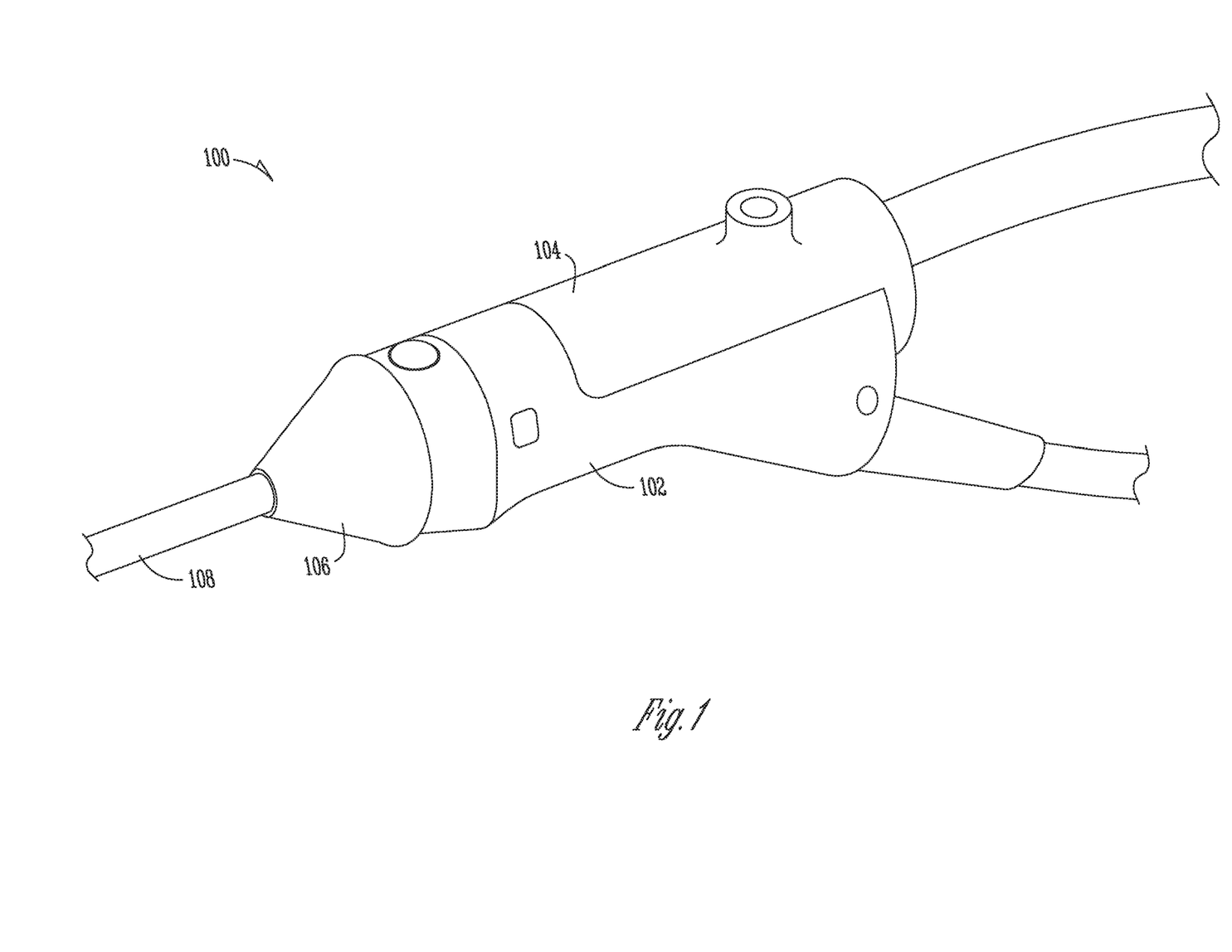
FIG. 1 illustrates a handheld surgical instrument in accordance with at least one example of the present disclosure.

Now making reference to the Figures, and more specifically FIG. 1, a handheld surgical instrument 100 is shown in accordance with at least one example of the present disclosure. The handheld surgical instrument 100 can include a handpiece 102, a tube set 104, and a cutting assembly 106 that can include a cutting implement 108. The cutting implement 108 can be a burr or a blade. In an example, the handheld surgical instrument 100 can be a microdebrider that can be used to treat various rhinological conditions, such as chronic rhinosinusitis, a deviated septum, nasal polyps, or the like. In an example, the handheld surgical instrument 100 can be a drill that can be used in Otologic procedures to remove bone in, and around, the ear.

During use of the handheld surgical instrument 100, a surgeon can hold the handheld surgical instrument 100 at the handpiece 102 and can manipulate the handheld surgical instrument 100 via the handpiece 102. In various examples, the handpiece 102 can be formed of a material that can have a thermal conductivity in a range between about 1 W/m·K to about 18 W/m·K, such as a polymer material. Examples of materials that can be used include Therma-Tech™ Thermally Conducive Formulations available from PolyOne™, headquartered in Avon Lake, Ohio. In some examples, Therma-Tech™ may include polyphenylene sulfide (PPS), polybutylene terephthalate (PBT), or Nylon 66. As noted above, during use of prior art handheld surgical instruments, hot spotting can occur at a handpiece of the handheld surgical instrument. Here, forming the handpiece 102 with a material that can have a thermal conductivity greater than about 1 W/m·K, to about 18 W/m·K and preferably in a range of about 10 W/m·K to about 18 W/m·K can allow dissipation of the heat generated by a motor of the handheld surgical instrument 100 during use. As such, the material of the handpiece 102 can assist with reducing or minimizing hot spots in the handpiece 102.

Moreover, as will be detailed below, the handheld surgical instrument 100 can include a suction passage that allows for the passage of saline. A polymer material that can be used for the handpiece 102 can have a high electrical resistivity. Thus, using a polymer material for the handpiece 102 can act as an insulator to prevent electrical connection with potentially charged radio frequency saline that can pass through a suction passage of the handheld surgical instrument 100.

While the cutting assembly 106 is shown engaged with a generic cutting implement 108, the cutting implement 108 can be any type of blade that can be used for various procedures, such as functional endoscopic sinus surgery (FESS) procedures. The type of blades that can be used for the cutting implement 108 can include a standard blade with or without suction capability, bipolar and/or monopolar energy blades that can be used for hemostasis during a surgical procedure, or a rotatable blade. Moreover, the cutting implement 108 can be a straight blade, an angled blade, or a turbinate blade. In addition, while the cutting implement 108 is shown, the handheld surgical instrument 100 can also include a burr in place of the cutting implement 108 for FESS procedures, such as a diamond bullet burr, a diamond ball burr, a diamond tapered burr, a fluted barrel burr, or an angled burr. In addition, the handheld surgical instrument 100 can be used for procedures other than FESS procedures. (the burr operation is the highest probability that can cause the temperature rise in the motor due to high speed and torque required to cut hard tissues such as bones. The blades 25 k RPMs, have very minimal effect). In these examples, the handheld surgical instrument 100 can include a tonsil and adenoid blades and laryngeal blades. Moreover, in further examples, the handheld surgical instrument 100 can be used as a dental drill, as an ontology drill for ENT applications, or with a Dremel™.

Figure 2:
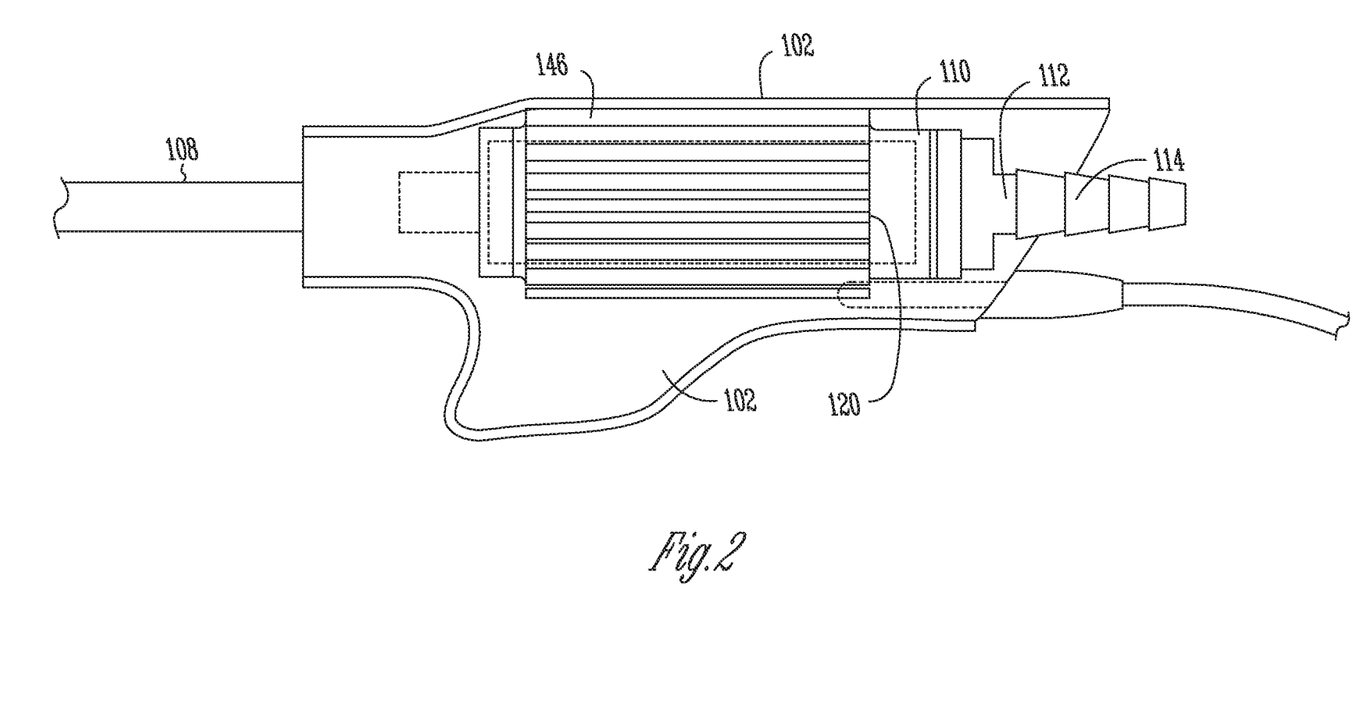
FIG. 2 illustrates a handpiece of the handheld surgical instrument shown with reference to FIG. 1 in accordance with at least one example of the present disclosure.
Figure 3:
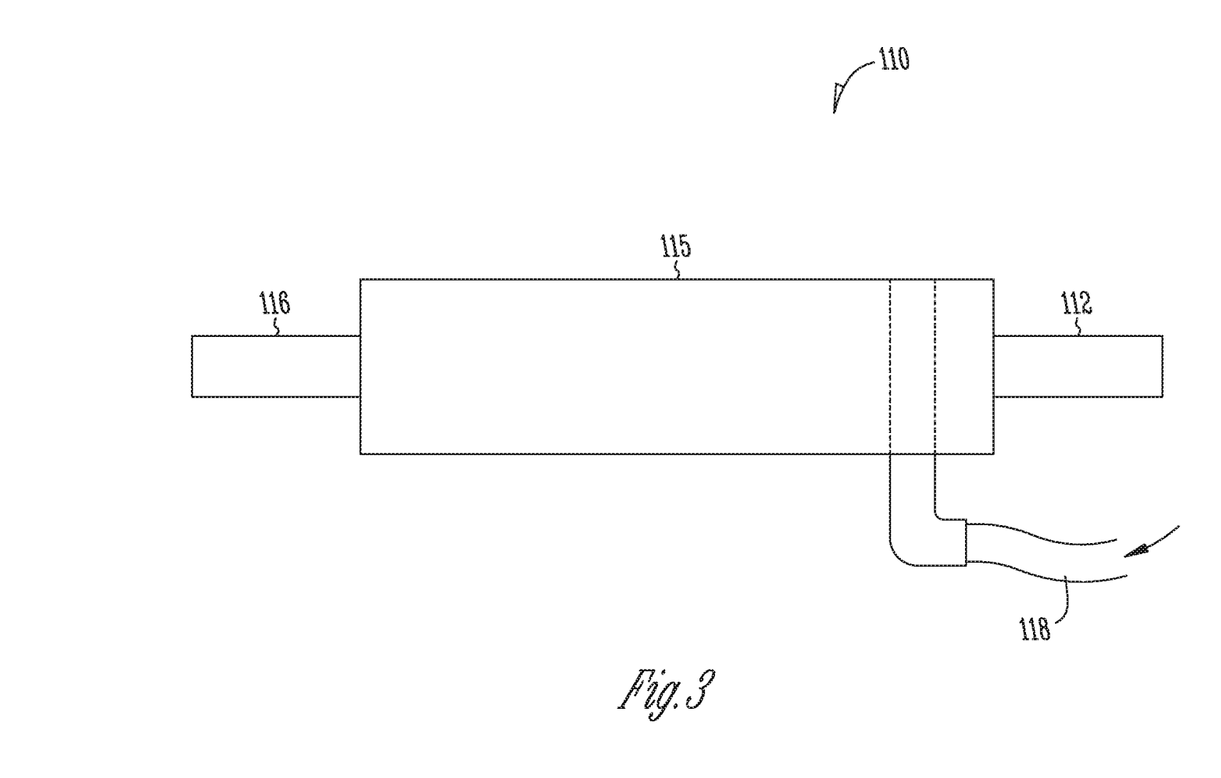
FIG. 3 shows a motor of the handheld surgical instrument in accordance with at least one example of the present disclosure.

Regardless of the type of cutting implement 108 used, the handheld surgical instrument 100 can include a motor 110 disposed within the handpiece 102 that can provide power to the handheld surgical instrument 100 and can actuate the cutting implement 108, as shown with reference to FIGS. 2 and 3. In accordance with an example of the present disclosure, the motor 110 can be a DC motor capable of rotating at speeds up to about 35,000 rpms or higher. In further examples of the present disclosure where the handheld surgical instrument 100 can function as a high speed drill, the motor 110 can be a DC motor capable of rotating at speeds up to about 100,000 rpms. In an example, the motor 110 can be cannulated to allow for the passage of components, such as a suction passage 112 from a suction connector 114, through the handpiece 102 and to a surgical site. As those skilled in the art will appreciate, the suction passage 112 can allow for suction at a surgical site during use of the handheld surgical instrument 100. Moreover, the suction passage 112 can allow for the passage of saline, such as RF saline, through the handheld surgical instrument 100 to a surgical site.

The motor 110 can also have a motor housing 115 along with a motor shaft 116 disposed within the motor housing 115 where the motor shaft 116 can be communicatively coupled to the cutting implement 108. In particular, the motor shaft 116 can include a proximal end disposed within the motor housing and a distal end where the distal end of the motor shaft 116 can be communicatively coupled to the cutting implement 108. In an example, the distal end of the motor shaft 116 can include a rotatable debrider, a microdebrider, a rotatable cutting implement, or the like. During operation, the motor 110 can rotate the motor shaft 116 within and with respect to the motor housing 115 such that the cutting implement 108 can be actuated during a surgical procedure. An electrical communication pathway 118 can provide current to the motor 110 such that the motor 110 can rotate the motor shaft 116 and can actuate the cutting implement 108 during operation of the handheld surgical instrument 100.

Figure 4:
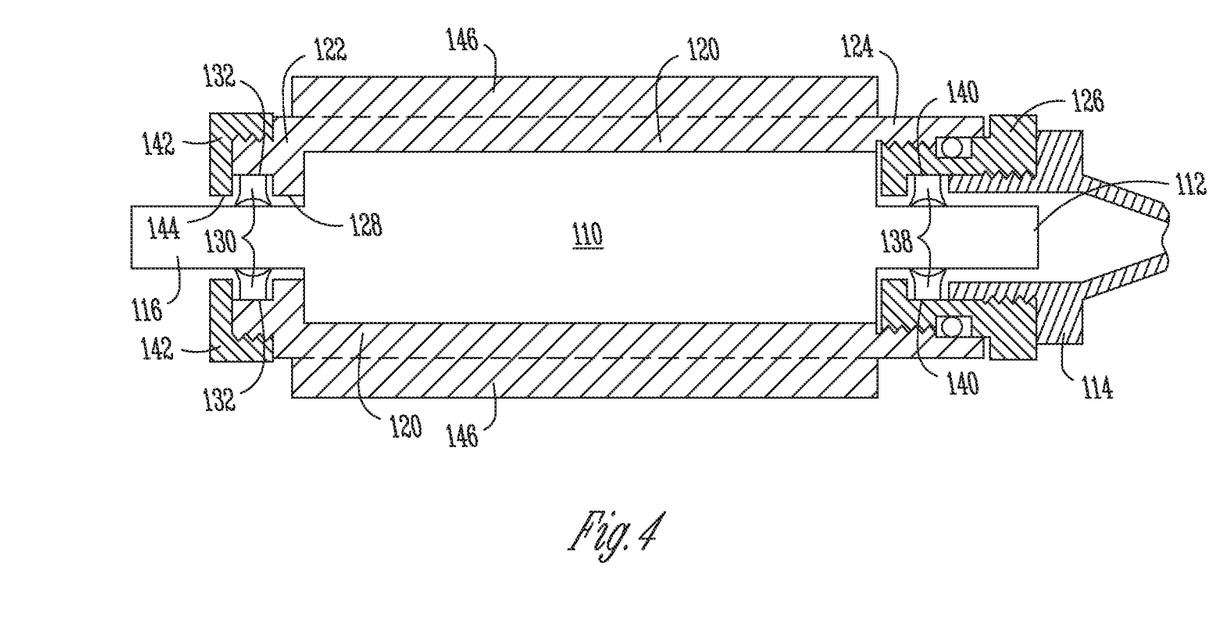
FIG. 4 illustrates a motor disposed within a heat sink in accordance with at least one example of the present disclosure.

In an example, the motor 110 can be disposed within a heat sink 120 that can substantially enclose the motor 110. In particular, the heat sink 120 can extend between a first end 122 and a second end 124 where the motor 110 can be disposed within the heat sink 120 between the first and second ends 122 and 124. When the motor 110 is placed within the heat sink 120, in addition to the first end 122, a coupling 126 can function to hold the motor 110 within the heat sink 120. The heat sink 120 can have an inner surface that is a substantially cylinder hollow.

In an example, the coupling 126 can threadingly engage with the heat sink 120 at the second end 124. Alternatively or in addition, the coupling 126 can be secured to the heat sink 120 using any other technique that can allow for secure engagement between the heat sink 120 and the coupling 126, such as a frictional fit, an adhesive, welding, a dovetail connection, or the like. The suction connector 114 can threadingly engage with the coupling 126 such that suction can be provided via the suction passage 112 during use of the handheld surgical instrument 100. Similar to the coupling 126, while the suction connector 114 is shown as being secured to the coupling 126 via threaded engagement, the suction connector 114 can be secured to the coupling 126 using any other technique that allows for secure engagement between the suction connector 114 and the coupling 126, such as a frictional fit, an adhesive, welding, a dovetail connection, or the like. As previously mentioned, the motor 110 can be cannulated. In examples where the motor 110 is cannulated, the suction connector 114 can provide suction via the suction passage 112 through the motor 110.

Figure 5:
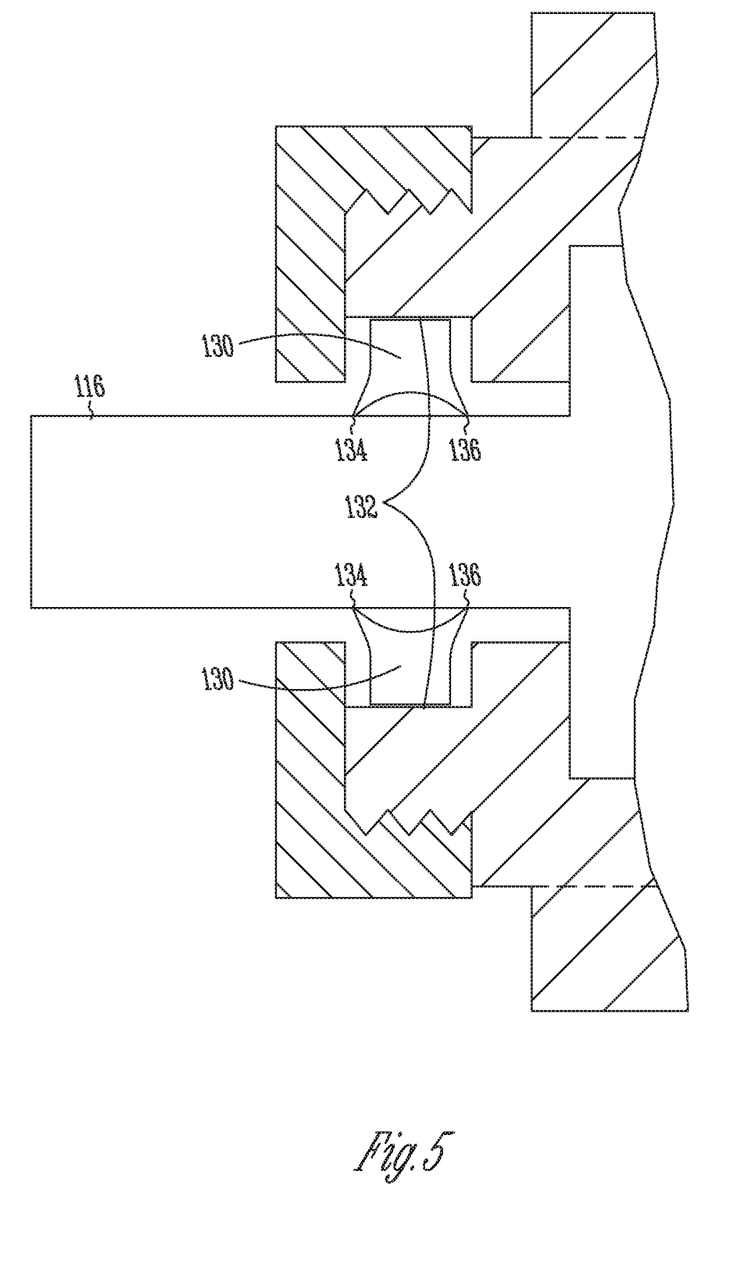
FIG. 5 shows a double-lip seal engaged with a motor shaft of the motor shown with reference to FIG. 4 in accordance with at least one example of the present disclosure.

As noted above, the motor can include the motor shaft 116. In order to accommodate the motor shaft 116, the heat sink 120 can include an opening or passage through which the motor shaft 116 can pass, such as the heat sink opening 128 shown in FIG. 4. Moreover, a seal 130 can sealingly engage with the motor shaft 116 at the heat sink opening 128 in order to seal the motor 110 within the heat sink 120. The seal 130 can be situated within a recess 132 of the heat sink 120 at the first end 122. The seal 130 can be any type of dynamic seal, such as a double-lip seal having a beveled edge. For example, as shown with reference to FIG. 5, the seal 130 can include seal edges 134 and 136 that can sealingly engage with the motor shaft 116 such that as the motor shaft 116 rotates during operation, the seal edges 134 and 136 can remain in contact with the motor shaft 116. The seal 130 can be formed from Viton™, any type of elastomer, fluoropolymer elastomer, or the like. In an example, the seal 130 can remain engaged with the motor shaft 116 via the seal edges 134 and 136 such that during reprocessing of the handheld surgical instrument 100, particulates, such as cleaning agents or any other type of fluids, do not enter the motor 110. In addition to the seal 130, other means can be used to seal the motor 110 with the heat sink 120, such as an o-ring or the like.

Returning attention to FIG. 4, the handheld surgical instrument 100 can include a seal 138 disposed in a recess 140 formed between the suction connector 114 and the coupling 126. The seal 138 can have characteristics that are similar to the seal 130. Thus, the seal 138 can be any type of dynamic seal, such as a double-lip seal having a beveled edge. Similar to the seal 130, the seal 138 can include seal edges that sealingly engage with the suction passage 112. The seal 138 can be formed from Viton™, any type of elastomer, fluoropolymer elastomer, or the like. The seal 138 can remain engaged with the suction passage 112 via the seal edges such that during reprocessing of the handheld surgical instrument 100, particulates, such as cleaning agents or any other type of fluids, do not enter the motor 110. In addition to the seal 138, other means can be used to seal the motor 110 with the heat sink 120, such as an o-ring or the like.

The handheld surgical instrument 100 can include a coupling 142 disposed near or adjacent to the first end 122. In an example, the coupling 142 can threadingly engage with the heat sink 120 at the first end 122, as shown with reference to FIG. 4. While the coupling 142 is described as being secured to the heat sink 120 via threaded engagement, the coupling 142 can be secured to the heat sink 120 using any other technique that allows for secure engagement between the heat sink 120 and the coupling 142, such as a frictional fit, an adhesive, welding, a dovetail connection, or the like. In order to allow the motor shaft 116 to engage with the cutting implement 108 or any other implement used with the handheld surgical instrument 100, the coupling 142 can include a coupling opening 144 through which the motor shaft 116 can pass when the motor 110 is disposed within the heat sink 120.

Figure 6:
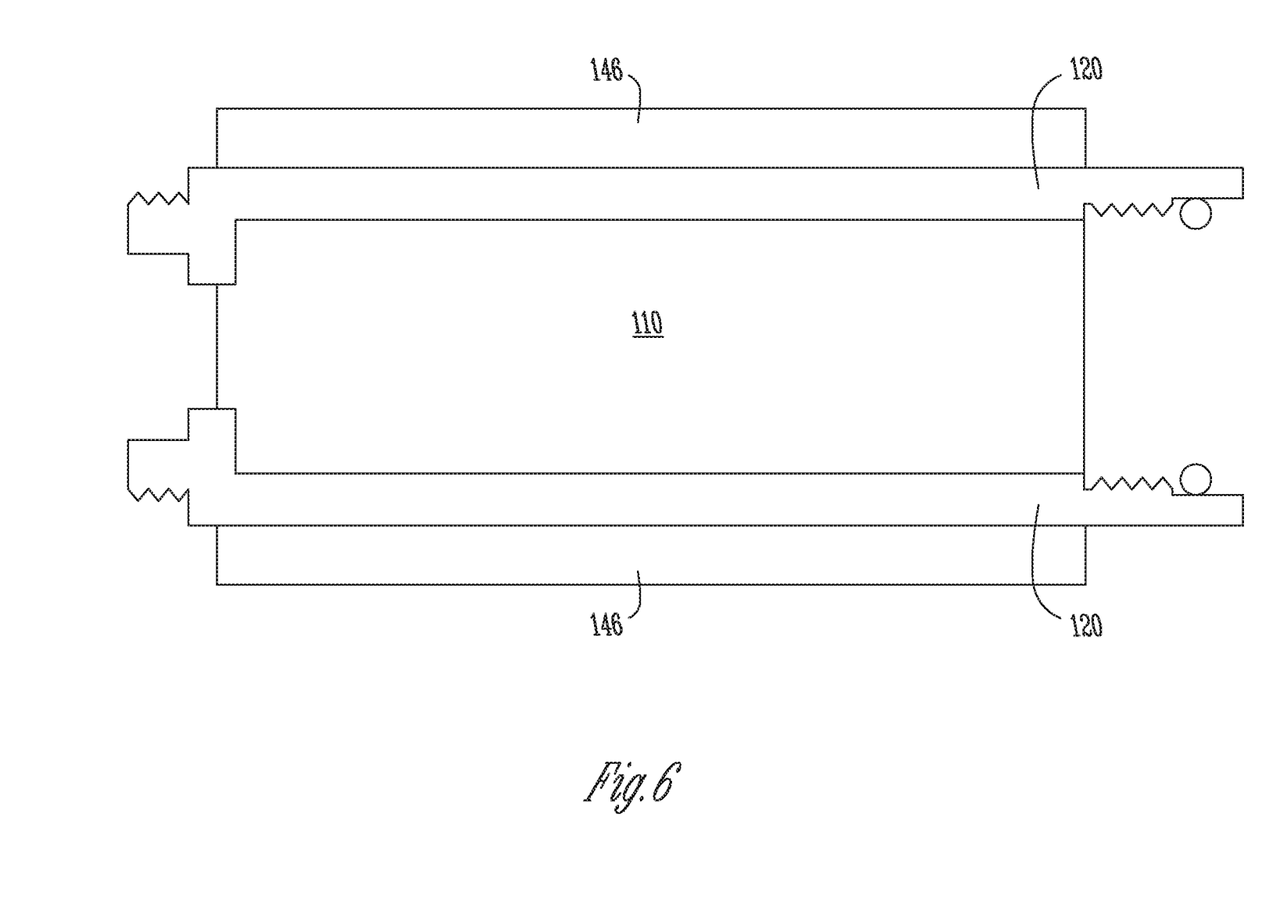
FIGS. 6 and 7 illustrate a heat sink and fins of the heat sink extending along the heat sink in accordance with at least one example of the present disclosure.
Figure 7:
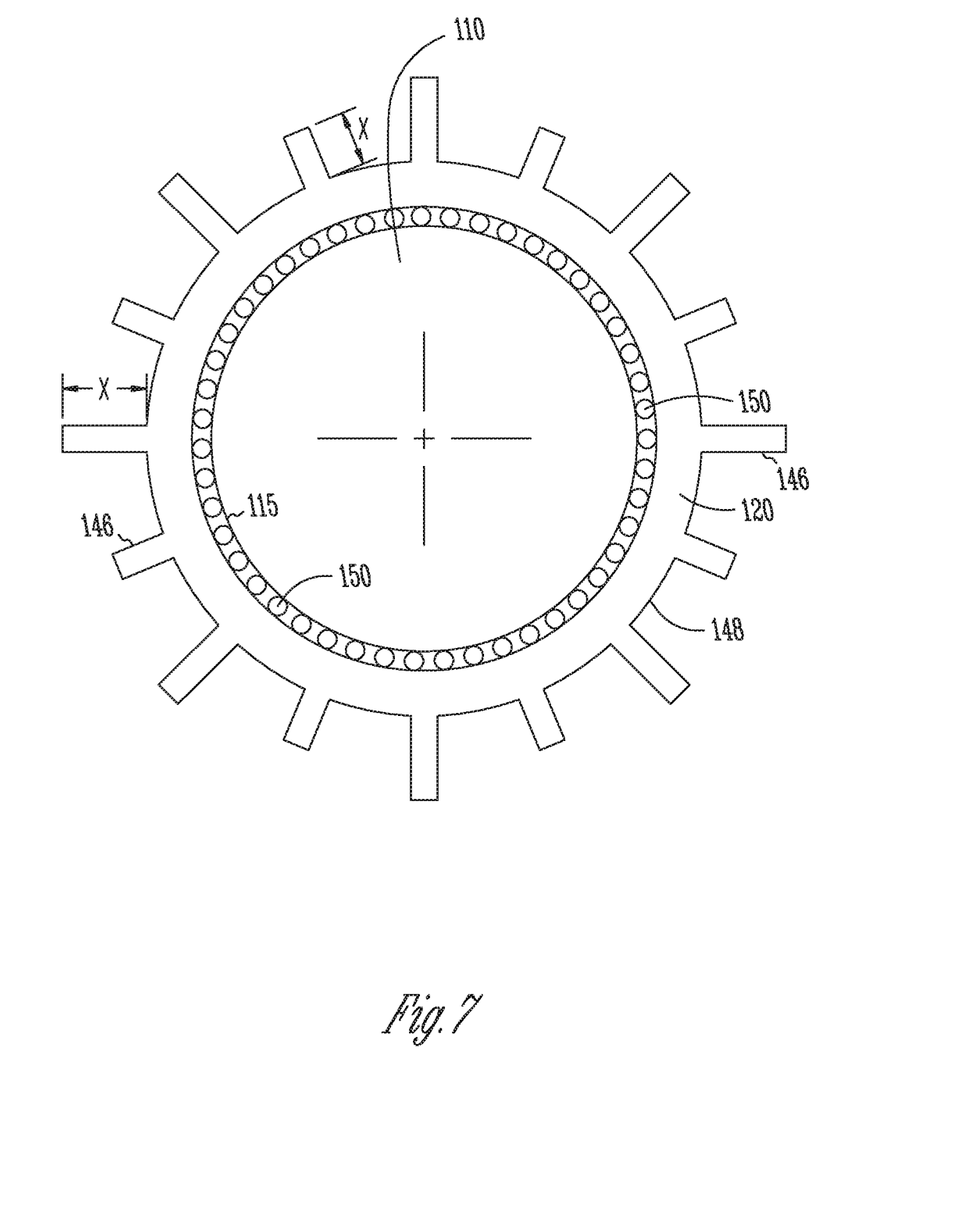

The heat sink 120 can be configured to dissipate heat generated by the motor 110 during operation of the motor 110. The heat sink 120 can include fins 146 that extend outwardly from a bottom surface of the heat sink 120, such as in a radial direction, as more clearly shown with reference to FIGS. 6 and 7. The fins 146 can extend along a desired length of the heat sink 120, such as a length equivalent to a length of the motor 110 as shown with reference to FIG. 6. Moreover, the fins 146 can extend outwardly in a radial direction from a heat sink surface 148 of the heat sink 120, as shown in FIG. 7. In some examples, the fins 146 can extend outwardly in a radial direction at different lengths X. In other examples, each of the fins 146 can extend outwardly in a radial direction at a same length. In some examples, one or more of the fins 146 can physically contact the handpiece 102 as shown with reference to FIG. 2 such that the fins 146 can be in thermal contact with the handpiece 102. In other examples, one or more of the fins 146 can be spaced apart from the handpiece 102 such that the fin does not physically contact the handpiece.

In some examples, the motor 110 can couple with the heat sink 120 using an adhesive putty 150. In particular, the adhesive putty 150 can be used during insertion of the motor 110 into the heat sink 120 where the adhesive putty 150 can thermally and physically couple the motor housing 115 with the heat sink 120. The adhesive putty 150 can ensure surface contact between the motor housing 115 and the heat sink 120. Specifically, the adhesive putty 150 can adhere an outer surface of the motor housing 115 to an inner surface of the heat sink 120. Moreover, using an adhesive putty 150 can obviate the need to use a keying mechanism or an anti-rotation feature. To further illustrate, a keying mechanism would require the heat sink 120 to have a flat surface formed in a circular surface of the heat sink 120. Moreover, a keying mechanism would require that the motor housing 115 have a flat surface formed in a circular surface that is complementary to the flat surface formed in the heat sink 120. Thus, the flat surface of the heat sink 120 can abut the flat surface of the motor housing 115. By virtue of each of the flat surfaces abutting each other, the motor housing 115 can couple with the heat sink 120. In an example, an adhesive putty 150 can have a thermal conductivity in a range of about 2.0 W/m·K to about 6.0 W/m·K. Furthermore, examples of an adhesive putty 150 that can be used can include Masterbond™ Supreme 10ANHT available from Masterbond™ headquartered in Hackensack, N.J., and LiPoly™ Thermally Conductive S-Putty available from Shiu Li Technology LLC having a U.S. headquarters in San Jose, Calif.

In addition to using the adhesive putty 150, other thermal materials can be used to couple the motor 110 with the heat sink 120. For example, a thermal adhesive can be used in place of the adhesive putty 150. An example of a thermal adhesive that can be used can include Loctite™ Stik 'N Seal™ available from Loctite Corporation having a global headquarters in Düsseldorf, Germany. Furthermore, other mechanisms can be used to couple the motor 110 with the heat sink 120. For example, the heat sink 120 can be press fit around the motor housing 115 or the heat sink 120 can be welded to the motor housing 115. Further examples can include a shim or a coupling between the motor housing 115 and the heat sink 120. In addition, a ball and detent assembly can be used between the motor housing 115 and the heat sink 120.

The heat sink 120 can be formed from any lightweight material having a high thermal conductivity, such as a thermal conductivity in a range between about 100 W/m·K to about 250 W/m·K. Examples can include aluminum, gold, nickel, silver, zinc, and the like. The fins 146 can be formed from the same material used for the heat sink 120 or from a different material having a suitable thermal conductivity. Furthermore, the couplings 126 and 142 can be formed from any lightweight material having a high thermal conductivity, such as a thermal conductivity in a range between about 100 W/m·K to about 250 W/m·K. Examples can include aluminum, gold, nickel, silver, zinc, and the like.

During operation of the motor 110, as noted above, the motor 110 can draw current from the electrical communication pathway, which increases an operating temperature of the motor 110. By virtue of the motor 110 and the heat sink 120 being in thermal contact, such as via the adhesive putty 150, the heat generated from the motor 110 can be dissipated to the heat sink 120 from the motor 110 according to the second law of thermodynamics. In an example where the heat sink 120 is formed from a material having a high thermal conductivity as discussed above, the heat can quickly dissipate through the heat sink 120 and to the fins 146. The fins 146 can transfer heat either through convection (when one or more of the fins 146 is spaced apart from the handpiece 102), conduction (when one or more of the fins 146 contacts the handpiece 102) to the handpiece 102, thermal radiation, or a combination thereof. As noted above, in some examples, the handpiece 102 can be formed of a material having a low thermal conductivity in a range of about 1 W/m·K to about 18 W/m·K and can allow for even heat distribution and dissipation throughout the handpiece 102 in order to avoid hot spotting, as discussed above.

The above detailed description includes references to the accompanying drawings, which form a part of the detailed description. The drawings show, by way of illustration, specific examples in which the invention can be practiced. These examples are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed. Description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

What is claimed is:

1. A handheld surgical instrument, comprising:
   a handpiece comprising a first material having a first thermal conductivity;
   a motor disposed within the handpiece and including a motor housing; and
   a heat sink disposed within the handpiece, the heat sink being thermally coupled to the motor housing, the heat sink comprising a second material having a second thermal conductivity that is greater in value than the first thermal conductivity;
   a first coupling; and
   a second coupling, wherein the heat sink includes a first end having external threads and a second end opposite the first end, the second end having internal threads, the external threads configured to engage with the first coupling and the internal threads configured to engage with the second coupling where the first and second couplings hold the motor within the heat sink.

2. The handheld surgical instrument of claim 1, further comprising a motor shaft, the motor shaft including:
   a proximal portion disposed within the motor; and
   a distal portion, wherein the distal portion of the motor shaft is coupled to a rotatable cutting implement.

3. The handheld surgical instrument of claim 1, wherein the heat sink is configured to completely enclose the motor.

4. The handheld surgical instrument of claim 1, further comprising a coupling configured to hold the motor within the heat sink.

5. The handheld surgical instrument of claim 1, wherein the first thermal conductivity is greater than or equal to approximately 1 W/m·K.

6. The handheld surgical instrument of claim 5, wherein the value of the second thermal conductivity is in a range between about 100 W/m·K and about 250 W/m·K.

7. The handheld surgical instrument of claim 1, wherein the first thermal conductivity is in a range between about 1 W/m·K to about 18 W/m·K and the value of the second thermal conductivity is in a range between about 100 W/m·K and about 250 W/m·K.

8. The handheld surgical instrument of claim 1, wherein the handpiece dissipates heat from the heat sink and the motor to reduce or minimize one or more hot spots on the handpiece.

9. The handheld surgical instrument of claim 1, further comprising an adhesive disposed between the motor housing and the heat sink.

10. The handheld surgical instrument of claim 1, wherein the heat sink has a plurality of fins radially extending from an outer surface of the heat sink, wherein a first fin of the plurality of fins extends a first distance from the heat sink outer surface and a second fin of the plurality of fins extends a second distance from the heat sink outer surface that is different from the first distance.

11. The handheld surgical instrument of claim 10, wherein one of the plurality of fins extends along a length of the heat sink that is substantially equal to a length of the motor and the one of the plurality of fins are thermally coupled with the handpiece.

12. The handheld surgical instrument of claim 10, wherein one of the plurality of fins are spaced apart from the handpiece such that the heat sink and the one of the plurality of fins dissipate heat via convection to the handpiece.

13. The handheld surgical instrument of claim 10, wherein one of the plurality of fins contact the handpiece such that the heat sink and the one of the plurality of fins dissipate heat via conduction to the handpiece.

14. A handpiece for a handheld surgical instrument, the handpiece comprising:
- a motor disposed within a motor housing, the motor and motor housing being partially disposed within the handpiece;
- a heat sink disposed about the motor housing within the handpiece and being thermally coupled to the motor housing, wherein the handpiece has a first thermal conductivity and the heat sink has a second thermal conductivity that is greater in value than the first thermal conductivity;
- a first coupling; and
- a second coupling, wherein the heat sink includes a first end having external threads and a second end opposite the first end, the second end having internal threads, the external threads configured to engage with the first coupling and the internal threads configured to engage with the second coupling where the first and second couplings hold the motor within the heat sink.

15. The handpiece of claim 14, further comprising an adhesive disposed between the motor housing and the heat sink.

16. The handpiece of claim 14, wherein the first thermal conductivity is in a range between about 1 W/m·K and about 18 W/m·K and the value of the second thermal conductivity is in a range between about 100 W/m·K and about 250 W/m·K.

17. The handpiece of claim 14, wherein the handpiece dissipates heat from the heat sink and the motor to minimize one or more hot spots on the handpiece.

18. A handpiece for a handheld surgical instrument, the handpiece comprising:
- a motor disposed within a motor housing, the motor and motor housing being partially disposed within the handpiece;
- a heat sink disposed about the motor housing within the handpiece and being thermally coupled to the motor housing, wherein the handpiece has a first thermal conductivity and the heat sink has a second thermal conductivity that is greater in value than the first thermal conductivity;
- a first coupling;
- a second coupling, wherein the heat sink includes a first end having external threads and a second end opposite the first end, the second end having internal threads, the external threads configured to engage with the first coupling and the internal threads configured to engage with the second coupling where the first and second couplings hold the motor within the heat sink; and
- an adhesive disposed between the motor housing and the heat sink, wherein the heat sink is configured to dissipate heat from the motor during operation of the motor.

* * * * *